United States Patent
Grimard et al.

(10) Patent No.: US 7,100,768 B2
(45) Date of Patent: Sep. 5, 2006

(54) PACKAGE FOR PRODUCTS TO BE STERILIZED WITH A HIGH-TEMPERATURE STERILIZING FLUID

(75) Inventors: Jean-Pierre Grimard, Vif (FR); Jean-Claude Thibault, Saint-Egreve (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/485,930

(22) PCT Filed: Nov. 16, 2001

(86) PCT No.: PCT/FR01/03614

§ 371 (c)(1),
(2), (4) Date: Feb. 2, 2004

(87) PCT Pub. No.: WO02/40065

PCT Pub. Date: May 23, 2002

(65) Prior Publication Data

US 2005/0103666 A1 May 19, 2005

(30) Foreign Application Priority Data

Nov. 20, 2000 (FR) .................................. 00 14976

(51) Int. Cl.
*A61B 17/06* (2006.01)
(52) U.S. Cl. ...................................... 206/438; 206/439
(58) Field of Classification Search ................ 206/438, 206/439, 363–370, 570–572, 63.3, 63.5, 206/484.1, 210; 215/271; 220/287, 359.1, 220/359.4
See application file for complete search history.

(56) References Cited

U.S. PATENT DOCUMENTS

| | | | | |
|---|---|---|---|---|
| 4,216,860 A | * | 8/1980 | Heimann | 206/370 |
| 4,466,552 A | * | 8/1984 | Butterworth et al. | 206/439 |
| 5,342,673 A | * | 8/1994 | Bowman et al. | 206/438 |
| 5,830,547 A | * | 11/1998 | MacKenzie et al. | 206/363 |
| 6,629,602 B1 | * | 10/2003 | Heyman | 206/366 |

FOREIGN PATENT DOCUMENTS

| | | | |
|---|---|---|---|
| EP | 266688 A2 | * | 5/1988 |
| JP | 09312354 A | * | 12/1997 |
| WO | WO 9111374 A2 | * | 8/1991 |

* cited by examiner

*Primary Examiner*—Mickey Yu
*Assistant Examiner*—J. Gregory Pickett
(74) *Attorney, Agent, or Firm*—David M. Fortunato

(57) ABSTRACT

The invention concerns a plastic package, having a content capable of being sterilised at high temperature, said package comprising at least a fluid communication member (16) between the inside and the outside of said package consisting of at least a frame circumscribing an opening and an inner seal (18) closing the opening, and whereof the peripheral edge (18a, 22a) continuously linked to said frame, said inner seal including, a selectively sealing material sheet whereof the cutoff threshold from outside inwards, stops contaminating particles and allows through the thermal sterilising fluid, said selectively sealing material being deformable in the plane of said sheet at said high temperature. The invention is characterised in that it comprises means compensating the planar deformation of the selectively sealing material sheet, when said inner seal (18) is in contact with the thermal sterilising fluid, said compensating means being designed to release at least part of the load in the direction opening the fluid communication member (16) applied on the frame as a result of said deformation.

6 Claims, 2 Drawing Sheets

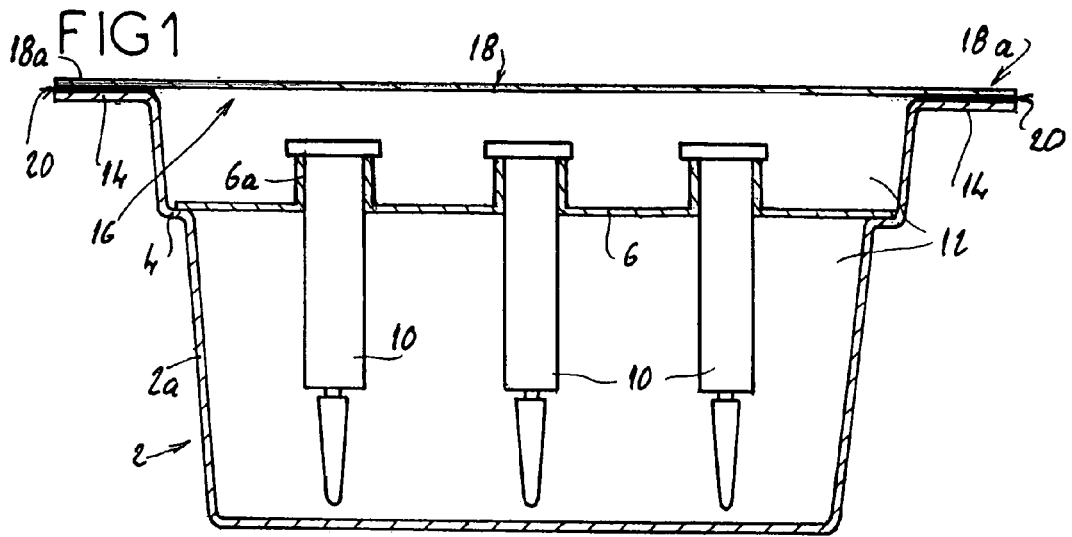
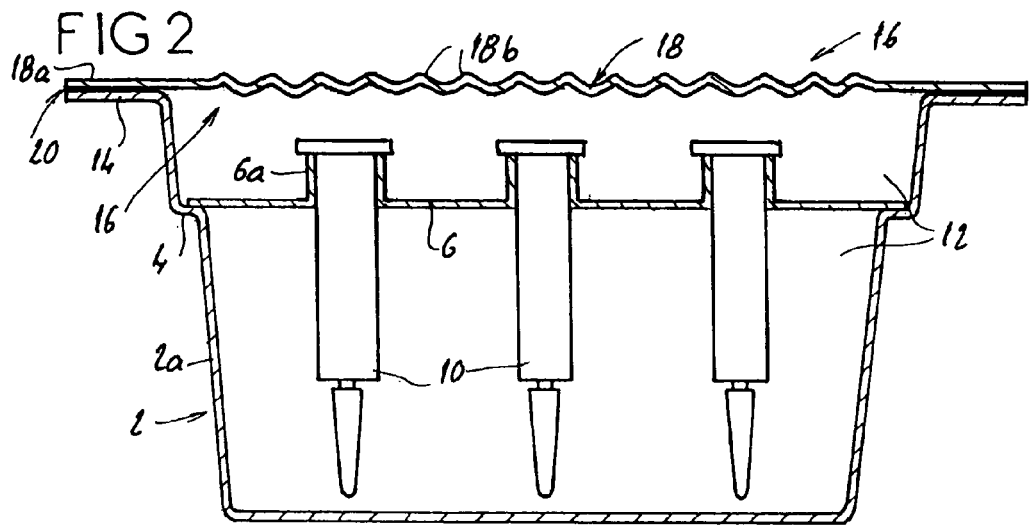
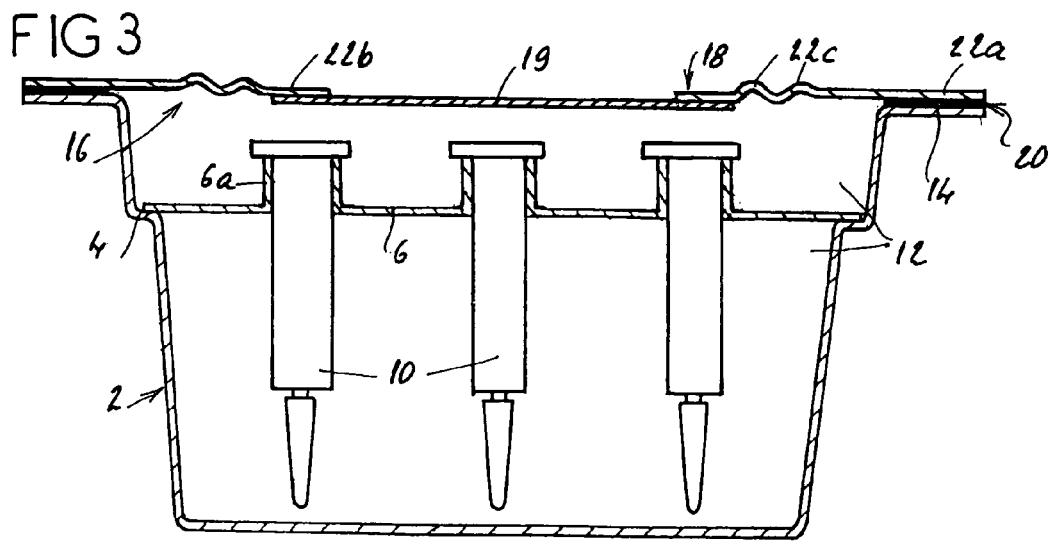

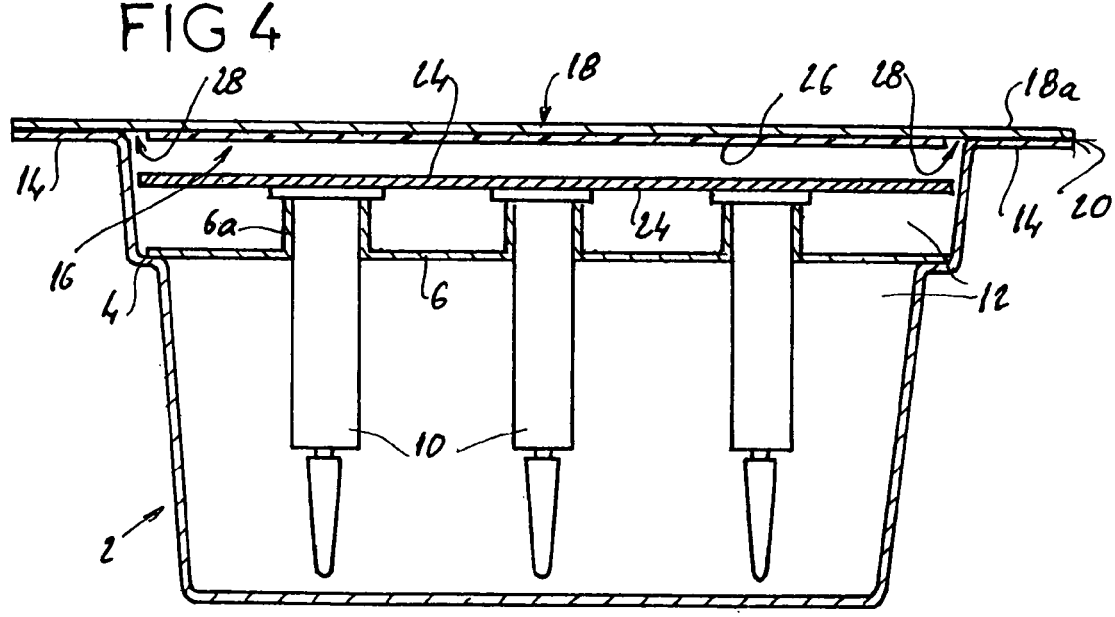

PACKAGE FOR PRODUCTS TO BE STERILIZED WITH A HIGH-TEMPERATURE STERILIZING FLUID

The present invention relates to the field of sterile or sterilized packaging, and more particularly to packaging intended to transport sterilized products or products intended to be sterilized.

The conditions of sterility in which certain stages of the handling or transportation of products or instruments intended for medical use are to be performed are extremely strict, particularly in the pharmaceutical industry. It is therefore extremely important to produce packaging compatible with such requirements.

In the remainder of the description, mention will be made of a certain number of expressions, which we need to define below.

The expression "selectively impervious material or sheet", as used in the present description and in the claims, is to be understood as meaning that the material is designed, in terms of structure, to control any exchange between the inside of the packaging and its external environment. This means, among other things, that the packaging is impervious, individually or in combination, to contamination by microorganisms, bacteria and/or a biologically active material which may come into contact with the packaging while it is being handled, while at the same time remaining permeable to a sterilization gas, for example ethylene oxide or a high-temperature thermal sterilizing fluid, for example steam.

The expressions "plastic" and "plastic material" are to be understood as meaning any material chosen from the polymer families such as styrenes, acrylics, polysulphones, polycarbonates, polyesters, polyolefines, etc., including copolymers, and polymer combinations and alloys.

The expression "high temperature" is to be understood as meaning temperatures close to the temperatures at which the plastic materials present deform.

Mention will also be made of a screen against electron irradiation, which is to be understood as meaning a material capable of absorbing the kinetic energy of the electrons from a beam and therefore of slowing these down or even preventing them from passing through the said material, or of reflecting the said electrons.

The expression "screen against light radiation" is to be understood as denoting any material which makes it possible to prevent light radiation, for example pulsed or ultraviolet, from passing through it.

The terms "transparent" and "opaque" are to be considered with respect to electron irradiation on the one hand and with respect to light radiation on the other hand. A material is transparent if light radiation or electrons can pass through it when it is subjected to electron irradiation. A material is therefore opaque to electron irradiation or to light radiation if it is able to absorb the kinetic energy of the electrons or to reflect them, or if it prevents light radiation from passing through it. The opacity and/or the transparency of a material are usually determined by a pair of parameters, namely the thickness and the density and, as appropriate, by the coefficient of reflection of electrons.

Packaging for sterile products or products intended to be sterilized by a gas of the ethylene oxide type and comprising a tub made of plastic and a cover made of a selectively impervious material, for sealing the said tub, is known.

Certain types of packaging, such as those used for transporting syringes before they are filled with an active product or a drug, are currently transported in plastic boxes, for example, made of polystyrene, covered with a cover sheet made of a selectively impervious material. The latter is, for example, a sheet based on filaments of HDPE (high density polyethylene) or some other polymer, bound together especially by heat and pressure. A product such as this, considered to be chemically inert, is marketed, for example, under the trademark TYVEK®.

Products intended to be sterilized are thus placed inside a tub, which is then sealed with the selectively impervious sheet. A sterilizing fluid then enters the tub through the sheet of selectively impervious material. The tub containing the sterile products is then placed in a protective bag so that it can be transported. The tub may also be placed in such a bag prior to the sterilization operation. In this case, the bag has a window covered with a material that is permeable to a sterilizing fluid.

By way of example, a tub or packaging such as this may contain syringes intended to be filled with a drug in a sterile room or controlled-environment room. Before the said syringes are filled, the protective bag needs to be opened and the packaging, which may be contaminated, needs to be decontaminated before it is taken, for example, into a sterile room. Such decontamination can be achieved using an electron beam developing enough energy that when it has passed through the cover sheet (selectively impervious material) it delivers a dose of radiation of, for example, 25 kGy. This means that it can be taken that the selectively impervious material has been decontaminated throughout its thickness, particularly in the sealed zone, at the interface between the tub and the said selectively impervious material.

This type of decontamination using an electron beam, may, however, exhibit drawbacks. This is because with decontamination using electron irradiation, electrons passing through the sheet of the selectively impervious material run the risk, on the one hand, of modifying or adversely affecting the material of which the syringes or products placed in the tub are made, for example glass, and, on the other hand, of using the oxygen in the air contained in the said tub to generate ozone. The latter can adversely affect rubber components or parts such as the caps on needles mounted on syringes, for example, or may pollute the atmosphere. Filling the syringes with a drug in a medium containing ozone may also be inadvisable.

The use of decontamination using light radiation is also not advisable because the said light radiation is generally not capable of passing through the sheet of selectively impervious material and therefore of reaching a zone located at the interface between the cover and the tub. This zone containing, for example, a layer of adhesive may exhibit irregularities and it is therefore essential to reach these irregularities, which may be contaminated, with a decontamination means.

It is known practice to produce packaging made of thermoplastic containing content that can be or has been sterilized by contact with a high-temperature thermal sterilizing fluid, the said packaging comprising at least one member for fluidic communication between the inside and the outside of the said packaging and consisting in at least one surround circumscribing an opening and a film closing the opening, and the peripheral border of which is constantly connected in sealed fashion to the said surround, the said film comprising a sheet of a selectively impervious material of which the cutoff threshold from the outside to the inside stops any contaminating particles and allows the passage of the thermal sterilizing fluid, the said selectively impervious material being capable, however, of deforming mainly in the plane of the said sheet at the said high temperature.

Packaging such as this may exhibit drawbacks.

Specifically, sterilization using a high-temperature sterilizing fluid, for example steam, may cause the selectively impervious material, for example the material known as TYVEK®, to shrink, which, given the relatively large dimensions of the tubs and packaging, gives rise to tension and deformation in the means of connection between the said sheet of selectively impervious material and the surround. Such tensions may give rise to deformation of the tub, and/or to detachment between the sheet of selectively impervious material and the said tub or the surround.

The objective of the present invention is to provide packaging for products that can be sterilized using a high-temperature thermal sterilizing fluid, which do not exhibit the drawbacks of the prior art, that is to say for which the use of a high-temperature thermal sterilizing fluid does not adversely affect the integrity of the said packaging.

Another objective of the invention is to provide packaging able, in addition to high-temperature sterilization, to undergo decontamination, for example using an electron beam or light or ultraviolet radiation.

According to the invention, the packaging comprises a means for compensating for the stresses and deformations of the tub and of the selectively impervious material when the said film is in contact with the thermal sterilizing fluid, the said compensation means being defined so that it at least partially relaxes the stress in the direction of the opening of the fluidic communication member applied to the surround as a result of the said deformations.

According to one embodiment of the packaging according to the invention, the selectively impervious material has a peripheral connecting zone over which an adhesive compatible with high-temperature sterilization is continuously spread, and a central zone which remains devoid of adhesive. The adhesive may also be spread discretely (successive spots of adhesive) and be converted into a continuous spread of adhesive after the sealing operation.

According to one embodiment of the packaging according to the invention, the compensation means is of the active type and consists in a shaping as a relief of the sheet of selectively impervious material, the developed surface area of which exceeds the visible surface area of the said sheet to such a point that, as it deploys, it cancels the omnidirectional stress associated with the planar shrinkage of the said sheet.

According to another embodiment according to the invention, the film comprises an edging of a material which is impervious to the thermal sterilizing fluid, the outer border of which is continuously connected in sealed manner to the surround of the fluidic communication member, and the inner border of which is continuously connected in sealed manner to the sheet of selectively impervious material, the said edging comprising the said compensation means.

According to another embodiment according to the invention, the compensation means is of the passive type and is capable of being obtained by thermal pretreatment of the selectively impervious material, definitively deforming it in a planar way.

Other features and advantages will also become apparent from the detailed description given hereinafter, given by way of example with reference to the appended drawing, in which:

FIG. 1 depicts, in section, one embodiment of packaging according to the invention;

FIG. 2 depicts, in section, another embodiment of packaging according to the invention;

FIG. 3 depicts, in section, an additional embodiment of packaging according to the invention;

FIG. 4 depicts, in section, an alternative form of embodiment of the packaging in FIG. 1.

The packaging according to the invention depicted in FIG. 1 comprises a plastic material produced in the form of a generally rigid tub 2 in which contents which can be or have been sterilized are placed. The tub 2 has an internal peripheral edge 4 on which there rests a support 6 which has shafts 6a in which syringes 10, for example, constituting the contents that can be or have been sterilized are engaged. The tub 2 thus delimits an internal volume 12. It also has an upper peripheral edge 14 extending roughly horizontally outwards. The packaging may thus receive at least one member 16 for fluidic communication between the inside and the outside of the said packaging.

The fluidic communication member 16 consists in at least one surround circumscribing an opening and a film 18 closing the said opening. The surround, which is rigid or semi-rigid, for example, consists, for example, of the upper peripheral edge 14. The film 18 has a peripheral edge 18a continuously connected in a sealed manner to the said surround and in this instance to the upper peripheral edge 14. This connection is obtained, for example, using a layer of adhesive 20. The film 18 comprises at least one sheet of a selectively impervious material whose cutoff threshold from the outside to the inside of the packaging stops any contaminating particles and allows the passage of a thermal sterilizing fluid.

The selectively impervious material comprises, for example, a sheet of a material known as TYVEK®. The latter is capable of shrinking, among other things, in the plane of the said sheet at a high temperature corresponding to a sterilization temperature. This temperature is, for example, from 121° C. to 130° C. when the sterilizing fluid is, for example, steam. The high-temperature thermal sterilizing fluid therefore enters the internal volume 12 by passing through the film 18. The adhesive 20 will preferably be chosen from solvent-free types, for example water-based or hot-melt adhesives.

The adhesive 20 will preferably be "peelable", that is to say will not generate particles or fibres when the film 18 is detached to open the tub 2.

The adhesive 20 is chosen so that any softening point it might have will be above the highest temperature reached during the sterilization operations.

The adhesive 20 makes it possible to produce a connection between the peripheral border 18a of the film 18 and the surround of the fluidic communication member 16. This connection is mechanically able to withstand the omnidirectional stress resulting mainly from the planar deformation of the sheet of selectively impervious material of which the film 18 is made.

According to one embodiment, the tub 2 has a wall 2a mechanically capable of withstanding the stress associated with the planar shrinkage of the sheet of selectively impervious material of which the film 18 is made.

The packaging according to the invention thus intrinsically comprises a means for compensating for the planar shrinkage of the sheet of selectively impervious material when the said film 18 is in contact with the fluid of a thermal sterilizer. The compensation means makes it possible to at least partially relax the stress in the direction of the opening of the fluidic communication member 16, which stress is applied to the surround as a result of the planar shrinkage.

According to another embodiment (also depicted diagrammatically in FIG. 1), the compensation means of the passive type can be obtained by a thermal pretreatment of the selectively impervious material by causing prior planar shrinkage thereof. The selectively impervious material is thus subjected to a high temperature, for example using a high-temperature fluid, for example steam passing through the said selectively impervious material. Irreversible shrinkage is thus obtained so that subsequent exposure to a high temperature (for example with the penetration of a high-temperature sterilizing fluid) avoids or minimizes additional shrinkage. The selectively impervious material, which has been pre-shrunk, thus maintains its dimensions and no detrimental additional stress occurs at the peripheral connection made between the peripheral border 18a and the upper edge 14.

According to another embodiment of the packaging according to the invention, the compensation means is of the active type (cf. FIGS. 2 and 3).

The embodiment depicted in FIG. 2 shows the compensation means consisting in a shape as a relief of the sheet of selectively impervious material of which the film 18 is formed. The developed surface area of this sheet of selectively impervious material exceeds the visible surface area of the said sheet to such an extent that, as it deforms or shrinks, it cancels the stress associated with the planar shrinkage of the said sheet. The shaping as a relief 18b is of the pleating, folding, embossing, corrugating or goffering type. This shaping of the relief also makes it possible to increase the surface area for exchange (passage of the sterilizing fluid) of the selectively impervious material.

In the example depicted in FIG. 3, the film 18 comprises an edging 22 of a material which may be impervious to the thermal sterilizing fluid, the outer border 22a of which is continuously connected in sealed manner to the surround of the fluidic communication member (upper peripheral edge 14). The inner border 22b of the edging 22 is continuously connected in sealed manner to the central sheet 19 of selectively impervious material. The connection between the central sheet 19 of selectively impervious material and the inner edge 22b of the edging 22 is obtained by any means, and in particular by the use of bonding. In this example, the edging 22 comprises the compensation means. The latter consists, for example, of another shaping as a relief 22c, for example folded, corrugated or pleated on itself, about one or more continuous lines circumscribing the central sheet 19 of selectively impervious material. The developed surface area of this edging 22 exceeds the visible surface area of the said edging 22 to such a point that, as it deforms, it cancels the stress associated with the planar isotropic shrinkage of the central sheet 19 of selectively impervious material.

According to one embodiment according to the invention, the material of which the edging 22 is made is transparent to sterilizing or decontaminating ultraviolet radiation.

The selectively impervious material is, for example, a nonwoven web of fibres or filaments of thermoplastic material, for example HDPE or some other polymer, entangled and joined together, for example by hot melting. The selectively impervious material may also consist of a material based on natural or plant fibres, of the paper type, which may have been treated or prepared in a special way if appropriate. The packaging according to the invention may also comprise at least one additional sheet 24 of selectively impervious material (cf. FIG. 4) resting over the syringes 10 and serving as additional mechanical protection and/or as additional screen for the said syringes 10. This additional sheet of selectively impervious material 24 may also be used in the embodiments depicted in FIGS. 1 to 3.

The film 18 comprises, for example, a first sheet of selectively impervious material (cf. FIG. 4) mounted on the tub 2 in the same way as described for the example of FIG. 1. This sheet of selectively impervious material is advantageously associated with a screen 26 against electron irradiation and/or visible and/or, for example, ultraviolet light radiation. The screen 26 may consist of one or more layers or sheets of additional selectively impervious material, which are therefore permeable to a high-temperature thermal sterilizing fluid.

This screen 26 may be attached to the film 18 by any known means, and in particular by bonding, or may be simply deposited onto the products 10 inside the tub 2 prior to the sealing of the latter. The screen 26 may also be made of an impervious material. In such a case, the dimensions of the screen 26 are chosen so as to form a peripheral zone 28, or other interruptions or orifices, on the sheet of the film 18, in direct communication with the interior volume 12. The high-temperature thermal sterilizing fluid thus enters the interior volume 12 by passing through this zone 28 of the sheet of selectively impervious material. The screen 26 consists, for example, of aluminium foil.

According to the invention, there is thus obtained a film 18 for the rigid packaging of sterilized products or products intended to be sterilized, comprising at least one sheet of a selectively impervious material of which the cutoff threshold from the outside toward the inside of the packaging stops all the contaminating particles and allows the passage of a high-temperature thermal sterilizing fluid. The film 18 also comprises the means for compensating for the deformation of the sheet of selectively impervious material upon contact with the high-temperature thermal sterilizing fluid. A film 18 such as this according to the invention may thus be manufactured separately and fitted to any type of packaging, preferably rigid packaging.

Other configurations or embodiments comprising a screen 26 (these are not depicted) may also be envisaged without departing from the scope of the present invention. The selectively impervious material may also be made of natural fibres, such as cellulose fibres, compatible with sterilization using steam, or alternatively a microperforated film.

A considerable advantage of the packaging according to the invention lies in its simplicity and in the possibility of using a sheet of the selectively impervious material, for example TYVEK®, whose use with high-temperature fluidic sterilization, particularly for large-size tubs 2, demands a certain amount of precautions.

Specifically, this is particularly true of tubs for which the ratio between the usable interior volume (in litres) and the surface area for the sealing of the film 18 on the tub 2 (in $dm^2$) is higher than 2 and more particularly still for those in which the ratio is higher than 3.

The use of a selectively impervious material for closing packages of dimensions as described above is therefore possible with high-temperature sterilization, and this is true for industrially and economically acceptable conditions.

The invention claimed is:

1. Packaging made of plastic containing content which can be or has been sterilized by contact with a high-temperature thermal sterilizing fluid, the said packaging comprising at least one member (16) for fluidic communication between the inside and the outside of the said packaging and consisting in a tub (2) and at least one surround circumscribing an opening and a film (18) closing the opening, and the peripheral border (18a, 22a) of which is constantly connected in sealed fashion to the said surround, the said film (18) comprising a sheet of a selectively impervious material of which the cutoff threshold from the outside to the inside stops contaminating particles and allows the passage of the thermal sterilizing fluid, the said selectively impervious material being capable of deforming mainly in the plane of the said sheet at the said high temperature, wherein said selectively impervious material has been thermally pretreated by definitively shrinking it in a planar way.

2. Packaging according to claim 1, characterized in that the selectively impervious material is a nonwoven web of fibres or filaments which are entangled and joined together.

3. Packaging according to claim 2, characterized in that the fibres or filaments are from a plastics material connected by thermofusion.

4. Packaging made of plastic containing content which can be or has been sterilized by contact with a high-temperature thermal sterilizing fluid, the said packaging comprising at least one member (16) for fluidic communication between the inside and the outside of the said packaging and consisting in a tub (2) and at least one surround circumscribing an opening and a film (18) closing the opening, and the peripheral border (18a, 22a) of which is constantly connected in sealed fashion to the said surround, the said film (18) comprising a sheet of a selectively impervious material of which the cutoff threshold from the outside to the inside stops contaminating particles and allows the passage of the thermal sterilizing fluid, the said selectively impervious material being capable of deforming mainly in the plane of the said sheet at the said high temperature, wherein said sheet includes a relief, said relief being defined by concentric adjacent portions of said sheet being disposed obliquely to the plane of said sheet in a pleat, fold, corrugation or goffer pattern.

5. Packaging made of plastic containing content which can be or has been sterilized by contact with a high-temperature thermal sterilizing fluid, the said packaging comprising at least one member (16) for fluidic communication between the inside and the outside of the said packaging and consisting in a tub (2) and at least one surround circumscribing an opening and a film (18) closing the opening, and the peripheral border (18a, 22a) of which is constantly connected in sealed fashion to the said surround, the said film (18) comprising a sheet of a selectively impervious material of which the cutoff threshold from the outside to the inside stops contaminating particles and allows the passage of the thermal sterilizing fluid, the said selectively impervious material being capable of deforming mainly in the plane of the said sheet at the said high temperature, and said film further comprising an edging (22) of a material which may or may not be impervious to the thermal sterilizing fluid, the outer border (22a) of which is continuously connected in sealed manner to the surround of the fluidic communication member (16), and the inner border (22b) of which is continuously connected in sealed manner to said sheet, wherein said edging includes a relief, said relief being defined by portions of said edging disposed in a pleat, fold, embossed, corrugation or goffer pattern.

6. Packaging according to claim 5, wherein said edging (22) is transparent to sterilizing or decontaminating ultraviolet radiation.

* * * * *